(12) United States Patent
Dunbar, Jr. et al.

(10) Patent No.: US 7,887,539 B2
(45) Date of Patent: Feb. 15, 2011

(54) SPINAL ROD APPROXIMATORS

(75) Inventors: William L Dunbar, Jr., Bethlehem, CT (US); Christopher Ryan Rybicki, Charlotte, NC (US); Ian Charles Burgess, Barrington, RI (US)

(73) Assignee: Depuy Spine, Inc., Raynham, MA (US)

( * ) Notice: Subject to any disclaimer, the term of this patent is extended or adjusted under 35 U.S.C. 154(b) by 375 days.

(21) Appl. No.: 10/761,036

(22) Filed: Jan. 20, 2004

(65) Prior Publication Data

US 2004/0147937 A1 Jul. 29, 2004

Related U.S. Application Data

(60) Provisional application No. 60/442,208, filed on Jan. 24, 2003.

(51) Int. Cl.
*A61B 17/58* (2006.01)

(52) U.S. Cl. .................. 606/86 A; 606/104; 606/916; 81/452

(58) Field of Classification Search .......... 606/104, 606/99, 61, 86 A, 916; 81/451–453
See application file for complete search history.

(56) References Cited

U.S. PATENT DOCUMENTS

| 410,780 | A | | 9/1889 | Cahn |
| 445,513 | A | | 1/1891 | Powell |
| 1,470,313 | A | | 10/1923 | Woolen |
| 1,628,144 | A | * | 5/1927 | Herrmann ............... 81/453 |
| 1,709,766 | A | * | 4/1929 | Bolton .................. 28/214 |
| 1,889,330 | A | * | 11/1932 | Humes et al. ............ 81/453 |
| 1,925,385 | A | * | 9/1933 | Humes et al. ............ 7/165 |
| 2,248,054 | A | * | 7/1941 | Becker ................... 81/457 |
| 2,248,057 | A | | 7/1941 | Becker |
| 2,291,413 | A | | 7/1942 | Siebrandt |
| 2,370,407 | A | * | 2/1945 | McCartney .............. 81/453 |
| 2,625,967 | A | * | 1/1953 | Stull .................... 81/57.42 |
| 2,800,820 | A | | 7/1957 | Retterath |
| 3,960,147 | A | | 6/1976 | Murray |
| 4,237,875 | A | * | 12/1980 | Termanini ............... 606/63 |
| 4,271,836 | A | | 6/1981 | Bacal |
| 4,411,259 | A | | 10/1983 | Drummond |
| 4,445,513 | A | | 5/1984 | Ulrich |
| 4,655,223 | A | | 4/1987 | Kim |
| 4,809,695 | A | | 3/1989 | Gwathmey |
| 4,896,661 | A | | 1/1990 | Bogert |
| 5,014,407 | A | | 5/1991 | Boughten |

(Continued)

FOREIGN PATENT DOCUMENTS

DE 4238339 5/1994

(Continued)

OTHER PUBLICATIONS

Sofamor, "Introducteur - Contreur De Tige" (schematic drawings), Jan. 1, 1994.
Sofamor "Introducteur—Contreur De Tige", Jun. 1994.

*Primary Examiner*—Eduardo C Robert
*Assistant Examiner*—Mary Hoffman

(57) ABSTRACT

Spinal rod approximator for seating a stabilizing rod in a rod-receiving portion of a spinal implant and inserting a closure mechanism is provided. In one embodiment, a spinal rod approximator is provided including a body with gripping branches, inserter shaft, threaded collar, and outer sleeve. The cylindrical outer sleeve is disposed about the distal end portion of the body and is movable between a first position and a second position in which the outer sleeve inhibits separation of the gripping branches.

10 Claims, 12 Drawing Sheets

U.S. PATENT DOCUMENTS

| | | |
|---|---|---|
| 5,020,519 A | 6/1991 | Hayes |
| 5,364,397 A | 11/1994 | Hayes |
| 5,391,170 A * | 2/1995 | McGuire et al. ............... 606/86 |
| 5,429,641 A * | 7/1995 | Gotfried ...................... 606/67 |
| 5,484,440 A | 1/1996 | Allard |
| 5,545,165 A | 8/1996 | Biedermann |
| 5,551,320 A | 9/1996 | Horobec |
| 5,616,143 A | 4/1997 | Schlapfer |
| 5,649,931 A * | 7/1997 | Bryant et al. ............... 606/104 |
| 5,697,933 A | 12/1997 | Gundlapalli |
| 5,707,371 A | 1/1998 | Metz Stavenhagen |
| 5,720,751 A | 2/1998 | Jackson |
| 5,725,532 A | 3/1998 | Shoemaker |
| 5,746,757 A | 5/1998 | McGuire |
| 5,782,831 A | 7/1998 | Sherman |
| 5,810,878 A | 9/1998 | Burel |
| 5,910,141 A | 6/1999 | Morrison |
| 5,951,564 A | 9/1999 | Schroder |
| 5,951,579 A | 9/1999 | Dykes |
| 6,010,509 A | 1/2000 | Delgado |
| 6,036,692 A | 3/2000 | Burel |
| 6,099,528 A | 8/2000 | Saurat |
| 6,123,707 A | 9/2000 | Wagner |
| 6,139,549 A | 10/2000 | Keller |
| 6,183,472 B1 | 2/2001 | Lutz |
| 6,210,330 B1 | 4/2001 | Tepper |
| 6,251,112 B1 | 6/2001 | Jackson |
| 6,258,090 B1 | 7/2001 | Jackson |
| 6,371,973 B1 | 4/2002 | Tepper |
| 6,440,133 B1 | 8/2002 | Beale |
| 6,440,142 B1 * | 8/2002 | Ralph et al. .................. 606/99 |
| 6,511,484 B2 * | 1/2003 | Torode et al. ............... 606/104 |
| 6,530,929 B1 | 3/2003 | Justis |
| 6,589,249 B2 | 7/2003 | Sater |
| 6,648,888 B1 | 11/2003 | Shluzas |
| 6,660,006 B2 | 12/2003 | Markworth |
| 6,726,692 B2 | 4/2004 | Bette |
| 6,743,231 B1 | 6/2004 | Gray |
| 6,746,449 B2 | 6/2004 | Jones |
| 6,752,832 B2 | 6/2004 | Neumann |
| 6,755,829 B1 | 6/2004 | Bono |
| 6,790,208 B2 | 9/2004 | Oribe |
| 6,790,209 B2 | 9/2004 | Beale |
| 6,827,722 B1 * | 12/2004 | Schoenefeld ............... 606/104 |
| 7,083,621 B2 | 8/2006 | Shaolian |
| 7,156,849 B2 | 1/2007 | Dunbar |
| 7,179,254 B2 | 2/2007 | Pendekanti |
| 7,179,261 B2 | 2/2007 | Sicvol |
| 7,278,995 B2 | 10/2007 | Nichols |
| 7,320,689 B2 | 1/2008 | Keller |
| 7,371,239 B2 | 5/2008 | Dec |
| 7,462,182 B2 | 12/2008 | Lim |
| 7,491,207 B2 | 2/2009 | Keyer |
| 7,527,638 B2 | 5/2009 | Anderson |
| 7,572,281 B2 | 8/2009 | Runco |
| 7,666,188 B2 | 2/2010 | Anderson |
| 7,708,763 B2 | 5/2010 | Selover |
| 2001/0029376 A1 | 10/2001 | Sater |
| 2002/0095153 A1 | 7/2002 | Jones |
| 2003/0028195 A1 | 2/2003 | Bette |
| 2003/0083747 A1 | 5/2003 | Winterbottom |
| 2003/0125750 A1 * | 7/2003 | Zwirnmann et al. ......... 606/104 |
| 2003/0149438 A1 | 8/2003 | Nichols |
| 2003/0191370 A1 | 10/2003 | Phillips |
| 2003/0199872 A1 | 10/2003 | Markworth |
| 2003/0225408 A1 | 12/2003 | Nichols |
| 2004/0036254 A1 | 2/2004 | Patton |
| 2004/0049191 A1 | 3/2004 | Markworth |
| 2004/0147936 A1 | 7/2004 | Rosenberg |
| 2004/0147937 A1 | 7/2004 | Dunbar |
| 2004/0172057 A1 | 9/2004 | Guillebon |
| 2004/0176779 A1 | 9/2004 | Casutt |
| 2004/0220567 A1 | 11/2004 | Eisermann |
| 2004/0254576 A1 | 12/2004 | Dunbar |
| 2004/0267275 A1 | 12/2004 | Cournoyer |
| 2005/0015095 A1 | 1/2005 | Keller |
| 2005/0055031 A1 | 3/2005 | Lim |
| 2005/0059969 A1 | 3/2005 | McKinley |
| 2005/0079909 A1 | 4/2005 | Singhaseni |
| 2005/0090824 A1 | 4/2005 | Shluzas |
| 2005/0131408 A1 | 6/2005 | Sicvol |
| 2005/0131420 A1 | 6/2005 | Techiera |
| 2005/0131422 A1 | 6/2005 | Anderson |
| 2005/0143749 A1 | 6/2005 | Zalenski |
| 2005/0149036 A1 | 7/2005 | Varieur |
| 2005/0149048 A1 | 7/2005 | Leport |
| 2005/0149053 A1 | 7/2005 | Varieur |
| 2005/0192570 A1 | 9/2005 | Jackson |
| 2005/0192579 A1 | 9/2005 | Jackson |
| 2005/0228392 A1 | 10/2005 | Keyer |
| 2005/0261702 A1 | 11/2005 | Oribe |
| 2006/0009775 A1 | 1/2006 | Dec |
| 2006/0025768 A1 | 2/2006 | Iott |
| 2006/0036254 A1 | 2/2006 | Lim |
| 2006/0036260 A1 | 2/2006 | Runco |
| 2006/0074418 A1 | 4/2006 | Jackson |
| 2006/0079909 A1 | 4/2006 | Varieur et al. |
| 2006/0089651 A1 | 4/2006 | Trudeau |
| 2006/0095035 A1 | 5/2006 | Jones |
| 2006/0111730 A1 | 5/2006 | Hay |
| 2006/0166534 A1 | 7/2006 | Brumfield |
| 2006/0166535 A1 | 7/2006 | Brumfield |
| 2006/0293692 A1 | 12/2006 | Whipple |
| 2007/0093849 A1 | 4/2007 | Jones |
| 2007/0129731 A1 | 6/2007 | Sicvol |
| 2007/0161998 A1 | 7/2007 | Whipple |
| 2007/0167954 A1 | 7/2007 | Sicvol |
| 2007/0173831 A1 | 7/2007 | Abdou |
| 2007/0213722 A1 | 9/2007 | Jones |
| 2007/0233097 A1 | 10/2007 | Anderson |
| 2007/0260261 A1 | 11/2007 | Runco |
| 2008/0077134 A1 | 3/2008 | Dziedzic |
| 2008/0077135 A1 | 3/2008 | Stad |
| 2008/0243190 A1 | 10/2008 | Dziedzic |
| 2008/0255574 A1 | 10/2008 | Dye |
| 2009/0030419 A1 | 1/2009 | Runco |
| 2009/0030420 A1 | 1/2009 | Runco |
| 2009/0054902 A1 | 2/2009 | Mickiewicz |
| 2009/0082811 A1 | 3/2009 | Stad |
| 2009/0088764 A1 | 4/2009 | Stad |
| 2009/0138056 A1 | 5/2009 | Anderson |
| 2009/0143828 A1 | 6/2009 | Stad |
| 2010/0137915 A1 | 6/2010 | Anderson |

FOREIGN PATENT DOCUMENTS

| | | |
|---|---|---|
| DE | 29806563 | 4/1998 |
| EP | 0948939 | 3/1999 |
| EP | 1574175 | 9/2005 |
| EP | 1648320 | 4/2006 |
| EP | 1796564 | 6/2007 |
| FR | 2677242 | 12/1992 |
| FR | 2729291 | 7/1996 |
| WO | 9621396 | 7/1996 |
| WO | 2005006948 | 4/2005 |
| WO | 2006020443 | 2/2006 |

* cited by examiner

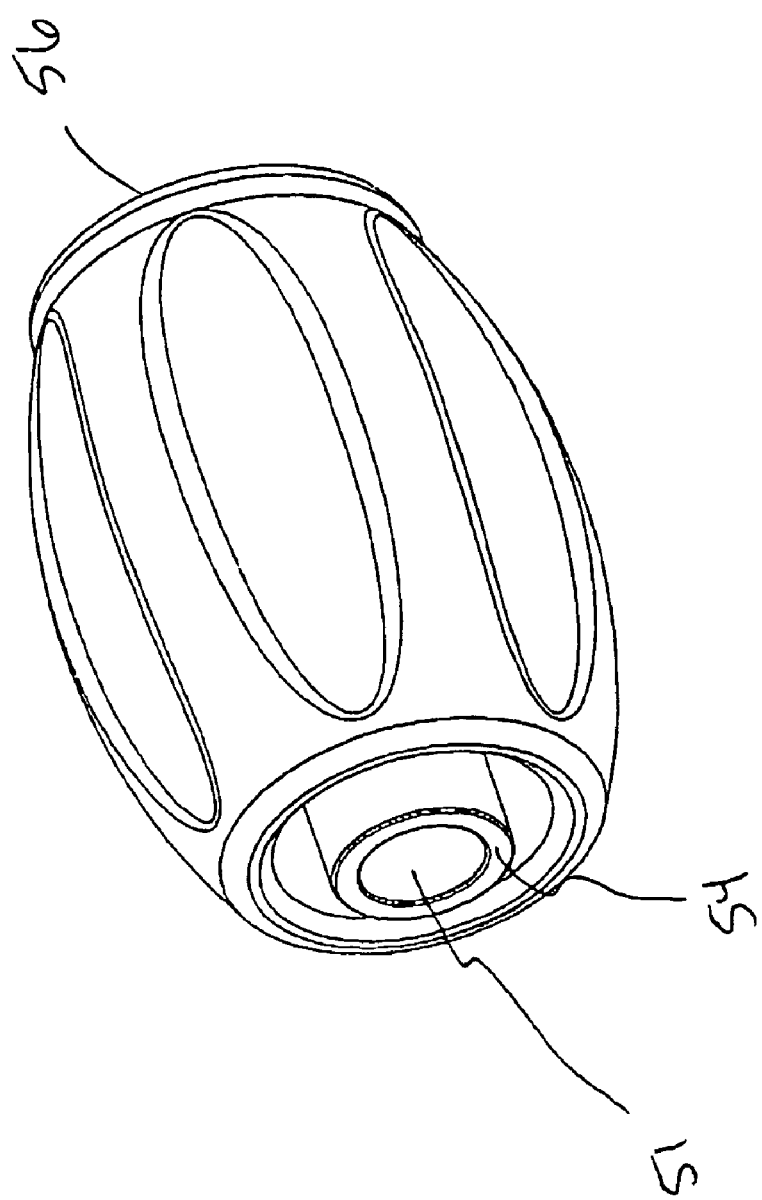

SPINAL ROD APPROXIMATORS

RELATED INVENTION

This application claims priority of U.S. Provisional Application No. 60/442,208, filed Jan. 24, 2003, entitled Spinal Rod Approximator, which is incorporated herein by reference.

FIELD OF THE INVENTION

The present invention relates to spinal fixation systems, and in particular to a spinal rod approximator.

BACKGROUND OF THE INVENTION

Spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. The rods can have a predetermined contour that has been designed according to the properties of the target implantation site, and once installed, the rod holds the vertebrae in a desired spatial relationship, either until desired healing or spinal fusion has taken place, or for some longer period of time.

Spinal fixation devices can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a rod-receiving element, usually in the form of a U-shaped slot formed in the head. A set-screw, plug, cap or similar type of closure mechanism, is used to lock the rod into the rod-receiving portion of the pedicle screw. In use, the shank portion of each screw is then threaded into a vertebra, and once properly positioned, a fixation rod is seated through the rod-receiving portion of each screw and the rod is locked in place by tightening a cap or similar type of closure mechanism to securely interconnect each screw and the fixation rod. Other anchoring devices also include hooks and other types of bone screws.

While current spinal fixation systems have proven effective, difficulties have been encountered in mounting rods into the rod-receiving portion of various fixation devices. In particular, it can be difficult to align and seat the rod into the rod receiving portion of adjacent fixation devices due to the positioning and rigidity of the vertebra into which the fixation device is mounted. Thus, the use of a spinal rod approximator, also referred to as a spinal rod reducer, is often required in order to grasp the head of the fixation device, and reduce the rod into the rod-receiving portion of the fixation device.

While several rod approximators are known in the art, some tend to be difficult and very time-consuming to use. Accordingly, there is a need for an improved rod approximator and methods for seating a spinal rod in a rod-receiving portion of one or more spinal implants.

SUMMARY OF THE INVENTION

The present invention provides tools, medical devices and methods for seating a stabilizing rod in a rod-receiving portion of a spinal implant and inserting a closure mechanism for locking the rod to the spinal implant.

In one embodiment, the invention is directed to a tool for seating a spinal rod in a rod-receiving portion of a spinal implant. The tool has a body having a proximal end portion and a distal end portion. The distal end includes first and second flexible branches for gripping a spinal implant, such as a screw or hook. An inserter shaft having a distal end adapted to hold a closure mechanism for said implant is slidably received within the body. A threaded collar adapted to couple the body and inserter shaft such that the inserter shaft forces a spinal rod into the rod-receiving portion of the spinal implant. An outer sleeve is rotatably and slidably mounted onto the distal end of the body. The sleeve is movable between a first and second position wherein movement of the sleeve prevents the branches from spreading and separating from its grip on the implant.

In another embodiment the invention is directed to a method of seating a rod into a rod-receiving portion of a spinal implant. The steps include holding a tool having a body including first and second flexible branches for gripping the spinal implant, an inserter shaft slidably received within the body, the inserter shaft having a distal end adapted to hold a closure mechanism for the implant, and a threaded collar, adapted to couple the body and the inserter shaft. The operator slides the inserter shaft beyond the distal end of the body and attaches the closure mechanism. The closure mechanism is withdrawn into the body. The rod is positioned between the branches of the body. The flexible branches are expanded over the implant to securely grip the implant. The threaded collar is threaded onto the body advancing the inserter shaft and urging the rod into the implant. The inserter shaft is rotated to lock the closure mechanism to the spinal implant.

BRIEF DESCRIPTION OF THE DRAWINGS

The invention will be more fully understood from the following detailed description taken in conjunction with the accompanying drawings, in which:

FIG. 7 is a perspective view illustration of the threaded collar of the device shown in FIG. 1;

DETAILED DESCRIPTION OF THE INVENTION

In general, the present invention provides a spinal rod approximator for seating a stabilizing rod in a rod-receiving portion of a spinal implant. Typical spinal implants include pedicle screws (monoaxial and polyaxial), hooks, and other bone screws. The spinal rod approximator of the present invention is particularly effective in that it is easy to use, does not require significant force to operate, and is efficient, thereby reducing the time and expense necessary to perform spinal surgery.

In one embodiment, a rod approximator device is provided including a body for gripping the spinal implant, an inserter shaft for inserting the closure mechanism and seating the rod into the rod-receiving portion of the spinal implant, and a threaded collar for coupling the movements of the body and the inserter shaft. The device also includes an outer sleeve for locking the body to the spinal implant. The body has a gripping means located at its distal end effective to engage a spinal implant from the side or above. The inserter shaft fits within the interior channel of the body and is of sufficient length to extend beyond the body at the proximal and distal ends. The distal end of the inserter is adapted to grasp the closure mechanism. The outer sleeve is rotatably mounted around the outside of the body and is capable of sliding in a longitudinal direction along the axis of the body to prevent the gripping means from releasing the spinal implant during use of the tool.

The threaded collar couples the body and the inserter shaft such that as the collar is threaded along the body it pushes on the inserter shaft moving it through the body. The force generated by the threaded collar is effective to move the inserter shaft with the closure mechanism into contact with the rod and urge the rod into the rod-receiving portion of the spinal implant. Once the rod is seated into the spinal implant, the closure mechanism is locked into place by rotating the inserter shaft.

Figure 1:
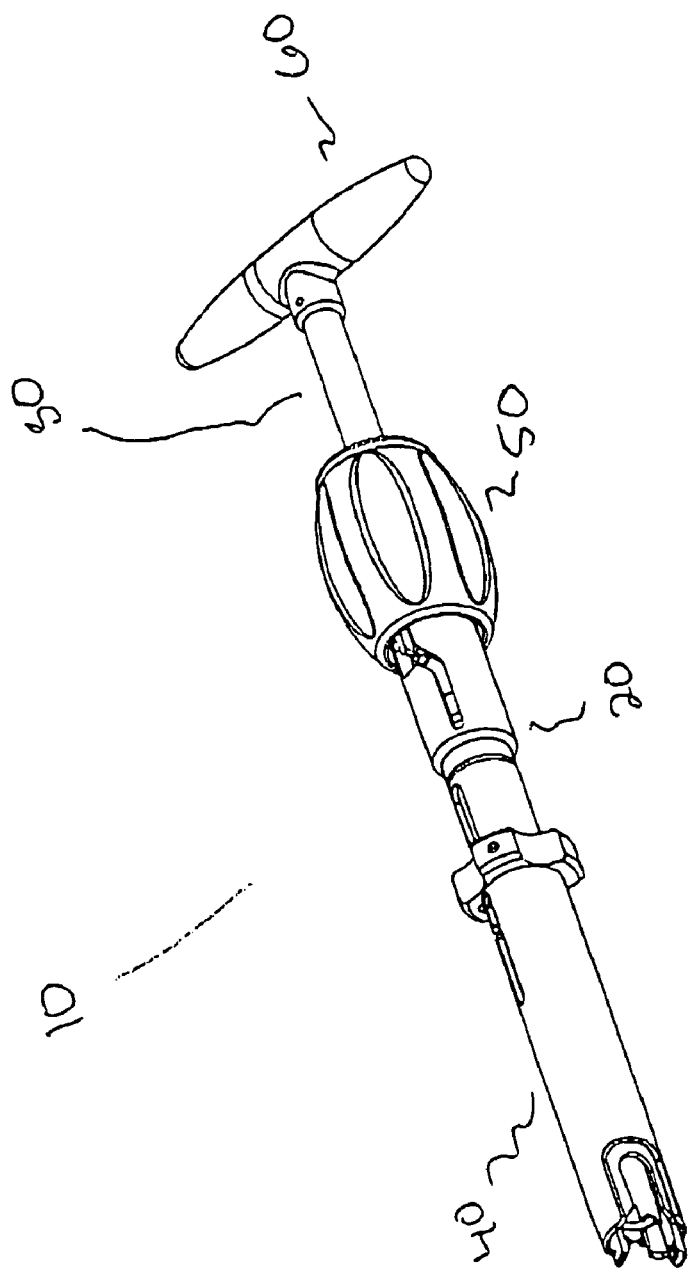
FIG. 1 is perspective view illustration of an assembled spinal rod approximator according to one embodiment of the present invention.
Figure 2:
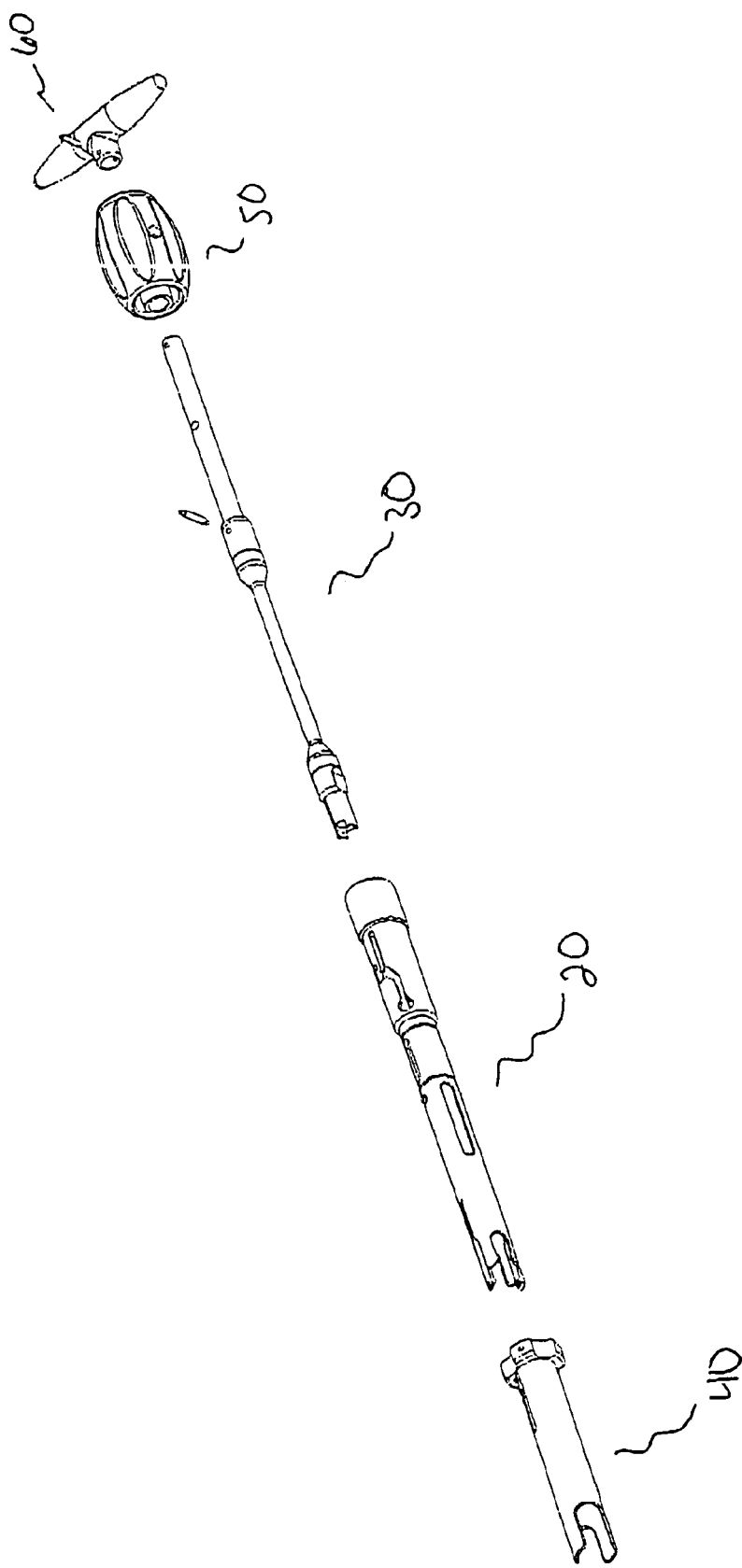
FIG. 2 is an exploded view illustration of the components that are assembled to form the device shown in FIG. 1.
Figure 3:
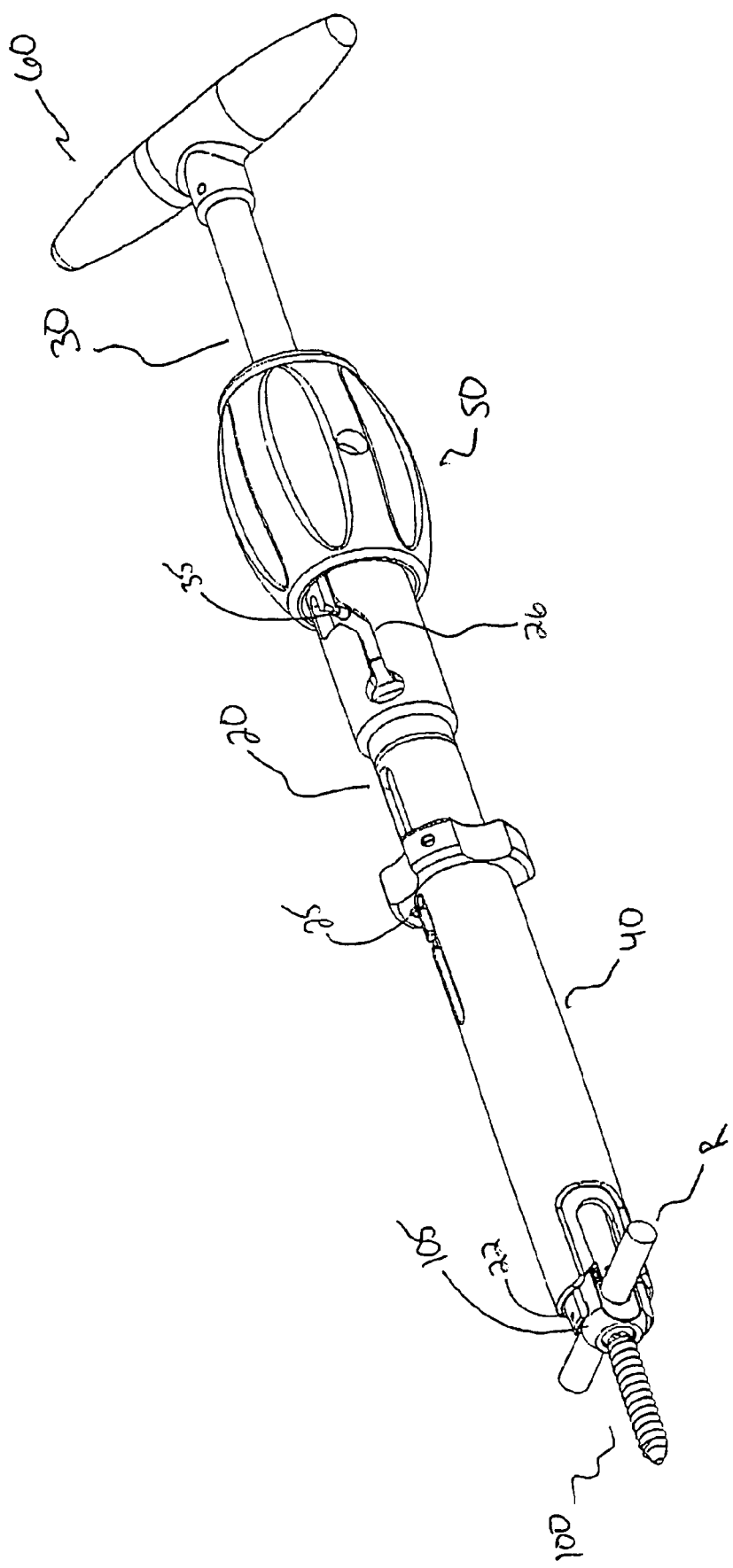
FIG. 3 is a perspective view illustration of the device shown in FIG. 1 gripping a spinal implant and a spinal rod.

FIG. 1 illustrates the preferred embodiment of an assembled spinal rod approximator 10 that is effective to engage and seat a stabilizing rod in a rod-receiving portion of a spinal implant. FIG. 2 illustrates the individual components that are assembled to form the spinal rod approximator. As shown, the tool 10 generally includes a body 20 having a gripping means 22 on the distal end, an inserter shaft 30 for inserting the closure mechanism, an outer sleeve 40 for preventing the gripping means from releasing from the spinal implant during use, and a threaded collar 50 for coupling the inserter shaft to the body. The tool performs several actions during its use. As shown in FIG. 3 the tool 10 holds the closure mechanism of the spinal implant on the distal end of the inserter shaft 30 as the gripping means 22 on the body grip the head 105 of the spinal implant 100 while capturing the spinal rod R, the threaded collar 50 advances the inserter shaft 30 to seat the spinal rod into the rod-receiving portion of the spinal implant, rotation of the T-handle 60 of the inserter shaft inserts the closure mechanism and locks it into place within the head of the spinal implant. The channel 26 on the body allows the user to visualize the steps as they occur from outside the surgical site.

A person having ordinary skill in the art will appreciate that while the tools and devices illustrated herein are described for use with spinal surgery, the tools can be adapted for use with a variety of medical procedures.

Figure 4:
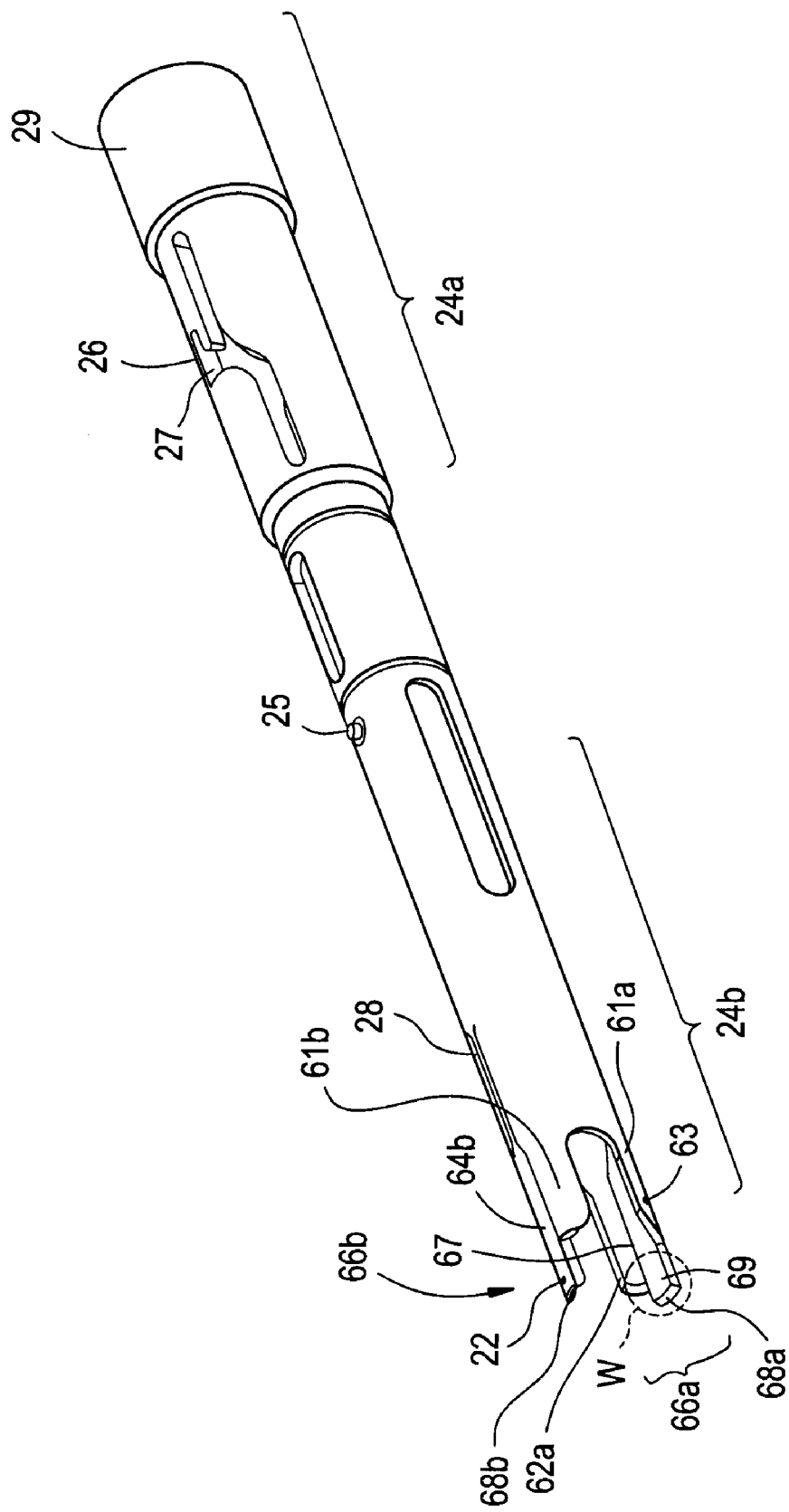
FIG. 4 is a perspective view illustration of the body of the device shown in FIG. 1.
Figure 5B:
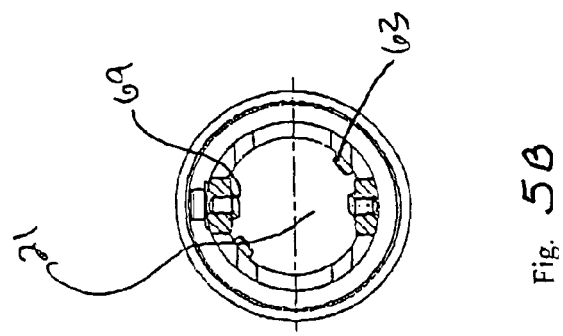
FIG. 5B is a cross-sectional view illustration of the body shown in FIG. 4 taken from the distal end.
Figure 5A:
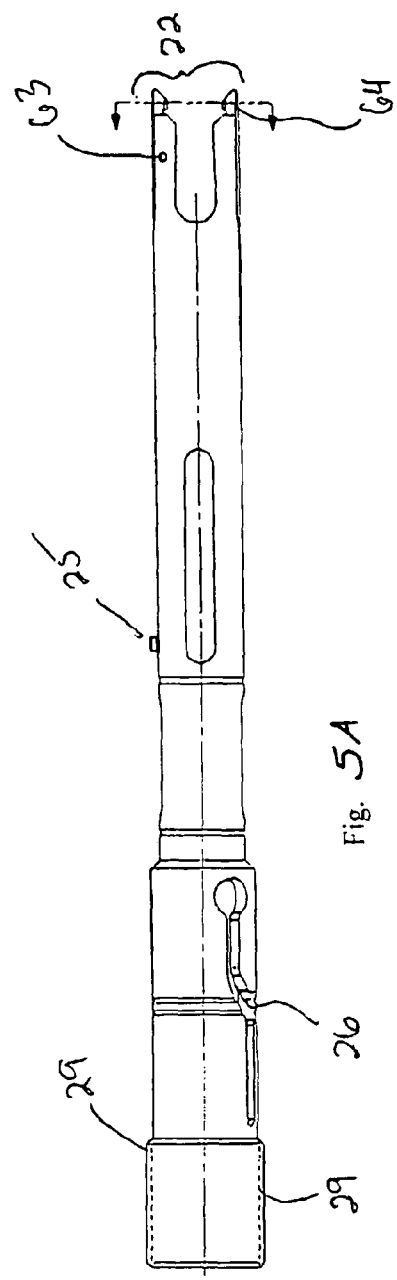
FIG. 5A is a side view illustration of the body shown in FIG. 4.

The body 20 of the rod approximator 10 is shown in more detail in FIGS. 4 through 5A. The body 20 can have a variety of shapes and sizes, but is preferably a generally longitudinal hollow tube having a proximal end portion 24a and a distal end portion 24b. The cross-sectional shape and size of the body 20, as well as the length of the body 20, can vary depending on the intended use. The body 20 should have a length sufficient to enable the distal end portion 24b of the body 20 to be placed adjacent a surgical site while the proximal end portion 24a of the body 20 remains outside a patient's body. By varying the size and shape, the body 20 can also be adapted for use in minimally invasive procedures.

The gripping means 22 include first and second branches 66a, 66b extending longitudinally from the distal end portion 24b of the body 20 and terminating in a distal end 68a, 68b. Each branch includes a flexible center 64a, 64b portion and two rigid side portions 61a, 62a, 61b, 62b. The center portion 64 is integrally formed from narrow slits 28 cut along the longitudinal axis of the distal end portion of the body. These slits provide the center portion the flexibility to expand around the implant head 105 to grip the implant and thus the slits permit branches 66a and 66b to be biased to a closed or gripping position. The center portion 64 forms the longest extension of the branch 66. Front rigid side portions 61a, 61b extend from the distal end portion 24b of the body along the center portion and terminate a distance from the distal tip of the center portion. The back rigid side portions 62a, 62b also extend from the distal end portion of the body and terminate just before the distal end of the center portion. The front and back rigid side portions 61, 62 form a substantially U-shaped recess to accommodate a spinal rod and spinal implant head. The distance from the distal end of the center portion 68 to the distal end of the front rigid side portion 61 is of sufficient length to allow the head of a spinal implant to pass through the channel to accommodate a side approach to gripping the spinal implant with the tool. The back rigid side portions 62 act as a stop to prevent the tool from completely passing over the spinal implant as the tool is gripping the implant from the side.

Preferably the interior surface 67 of each center portion 64 has a projection 69 for engaging a corresponding recess 103 located on the head of the spinal implant. Preferably a pin 63 projects from the interior surface 65 of the front rigid side portion 61. The pin 63 acts as a stop engaging the top surface 109 of the implant to prevent the tool from sliding down over the entire spinal implant when using the tool to grip the implant from above. FIG. 5A shows a cross-sectional view of the body 20 from the distal end. This view shows the interior channel 21 of the body and depicts the placement of the pins 63 and projections 69.

Each branch 66a, 66b can have virtually any shape and size, and the branches can include several different mating features to facilitate grasping of the implant. As shown, the opposed branches 66a, 66b have a generally elongate, rectangular shape and include opposed inner surfaces 67a, 67b. The opposed inner surfaces each preferably have the same inner diameter which is designed to mate with the outer diameter of the head of the spinal implant. The projection 69 is located at the distal end of the inner surface. The distal most end of each center portion 68 can be rounded to prevent any potential damage to tissue surrounding the treatment site as the tool is used to grip the spinal implant. The projections 69 on the center portions and/or the head of the spinal implant can also include a variety of mating elements, including tongue-and-groove connections, dovetail connections, etc.

Along the proximal end portion 24a of the body is a guide mechanism which in the preferred embodiment takes the shape of a channel 26 to control the axial translation and rotational orientation of the inserter shaft 30 during operation of the instrument. The guide mechanism also allows the surgeon to visualize the steps of operation from outside the surgical site as they occur. The channel runs parallel to the longitudinal axis of the body. A portion of the channel 27 branches at an angle from the main portion of the channel and reverses direction. This portion of the channel controls the rotational orientation of the shaft with respect to the body and provides for proper alignment of the closure mechanism when locking to the implant and allows for releasing of the closure mechanism after locking. In the preferred embodiment this branch angles away from the main channel at approximately 90 degrees.

The proximal end portion of the body has external threads 29 to mate with the threads of the threaded collar 50. The external threads 29 are illustrated in the side view of the body (FIG. 5) as a dashed line. Between the distal end portion and the proximal end portion of the body a pin 25 extends outward for engaging the outer sleeve 40.

Figure 6:
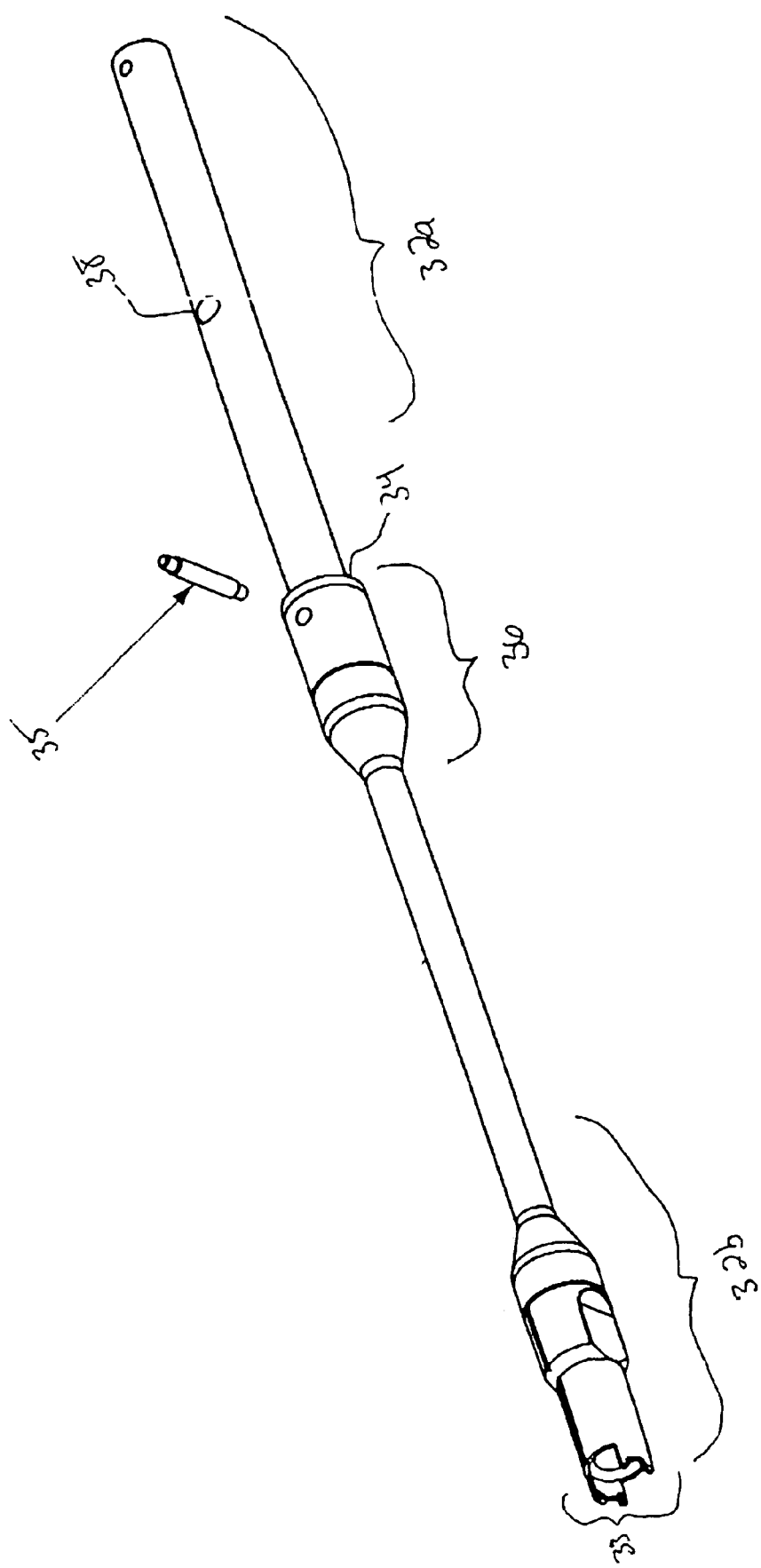
FIG. 6 is a perspective view illustration of the inserter shaft of the device shown in FIG. 1.
Figure 6A:
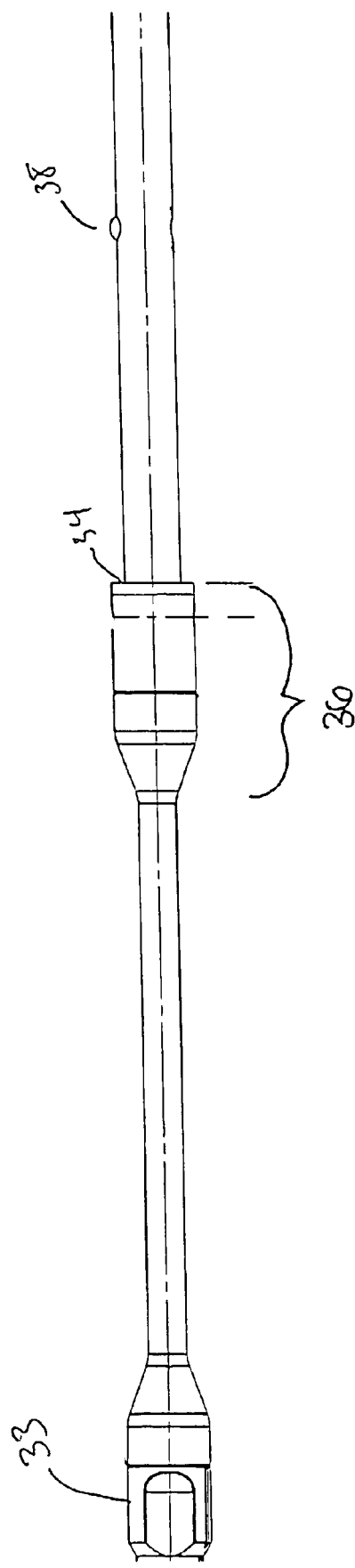
FIG. 6A is a cross-sectional view illustration of the inserter shaft shown in FIG. 6.

Referring now to FIG. 6 the inserter shaft 30 is sized to be slidably received within the interior channel 210f the body 20 and coupled to the body 20 by the threaded collar 50. The inserter shaft 30 can also have a variety of configurations, but is preferably a generally longitudinal body having a proximal end portion 32a and a distal end portion 32b. The length of the inserter shaft 30 can vary, but preferably the inserter shaft 30 has a length greater than the length of the body 20 such that it may extend beyond the distal and proximal ends of the body.

Located on the tip of the distal end portion 32b of the inserter shaft is the holder 33 for the spinal implant closure mechanism. The holder 33 can be adapted to hold the closure mechanism in a variety of ways. In the present invention the holder 33 uses a friction fit or press fit to hold the closure mechanism. By way of non-limiting example, the holder 33 can include flexible tabs (not shown) formed therein to snap onto the closure mechanism. A person having ordinary skill in the art will appreciate that virtually any holding technique can be used to engage the closure with the distal tip of the inserter shaft.

The proximal end portion 32a of the inserter shaft is connected to a T-handle 60. Located between the proximal and distal ends of the inserter shaft is a transition zone 36 where the shaft transitions to a larger cross-sectional diameter from the distal portion of the shaft. At the proximal end of the transition zone is a shoulder 34 which the threaded collar 50 engages to reduce the spinal rod into the rod-receiving portion of the spinal implant. Projecting out from the transition zone is a pin 35 which is co operable with the channel 26 on the body 20 to control the axial translation and rotational orientation of the inserter shaft with respect to the body. The pin travels within the channel tracking the steps of the inserter shaft 30 as it grasps the spinal implant closure mechanism, pushes against the rod, inserts the closure mechanism and locks it into place. Since the pin is visible through the channel, the user is able to visualize these steps as they occur from outside the surgical site. Along the channel are markings which indicate to the user when to perform each of these steps. The tool is assembled with the pin captured within the channel such that the inserter shaft is not removable from the body. The length of the channel limits the distance that the inserter can translate within the body. The distance between the channel and the branched portion 27 of the channel limits the amount the inserter can rotate within the body. This distance corresponds to the amount of rotation necessary to lock the closure mechanism in place.

A person having ordinary skill in the art will appreciate that virtually any guiding technique can be used to guide the inserter shaft within the body. For example, the pin could be located on the body and engage a channel on the inserter shaft.

A projection 38 is located on the surface of the inserter shaft between the proximal end portion and the shoulder. Projection 38 rests against the rim 56 at the proximal end of the threaded collar to prevent the inserter shaft from sliding down and extending beyond the distal end of the body after the closure mechanism has been picked up and prior to gripping to implant.

Figure 7A:
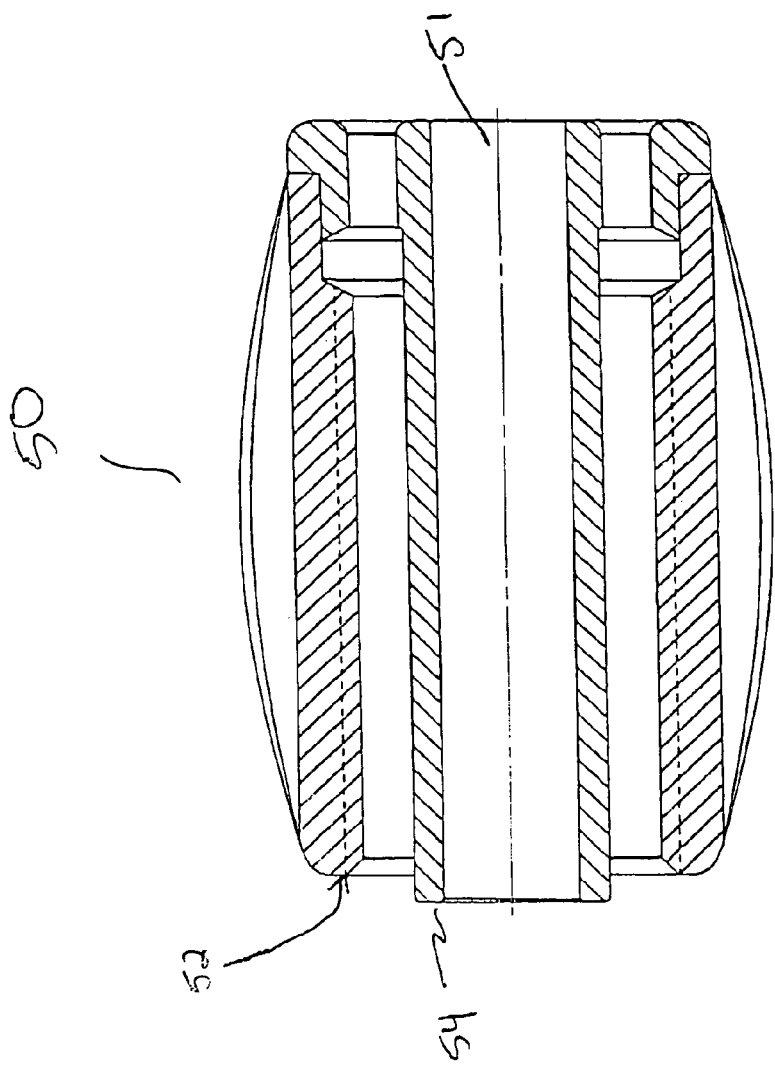
FIG. 7A is a cross-sectional view illustration of the threaded collar shown in FIG. 7.

Referring now to FIG. 7 and FIG. 7A, threaded collar 50 has a hollow body with internal threads 52 adapted to engage the external threads 29 of the body 20. Located within the threaded collar is a central shaft 51 having an internal diameter that is greater than the diameter of the proximal portion of the inserter shaft and less than the diameter of the shoulder 34 at the transition zone of the inserter shaft. The central shaft extends from the proximal end of the threaded collar. The distal rim 54 of the shaft projects beyond the distal end of the collar. The collar is rotatable and slidable along the proximal end portion of the inserter shaft 30 up to the transition zone. When the collar is advanced into contact with the body it is threaded onto the external threads 29 of the body 20, such that the distal rim 54 of the center shaft engages the shoulder 34 of the inserter shaft 30 to push the closure mechanism held by the distal end 33 of the inserter shaft against a spinal rod to seat the rod in the rod-receiving portion of the implant.

Figure 8:
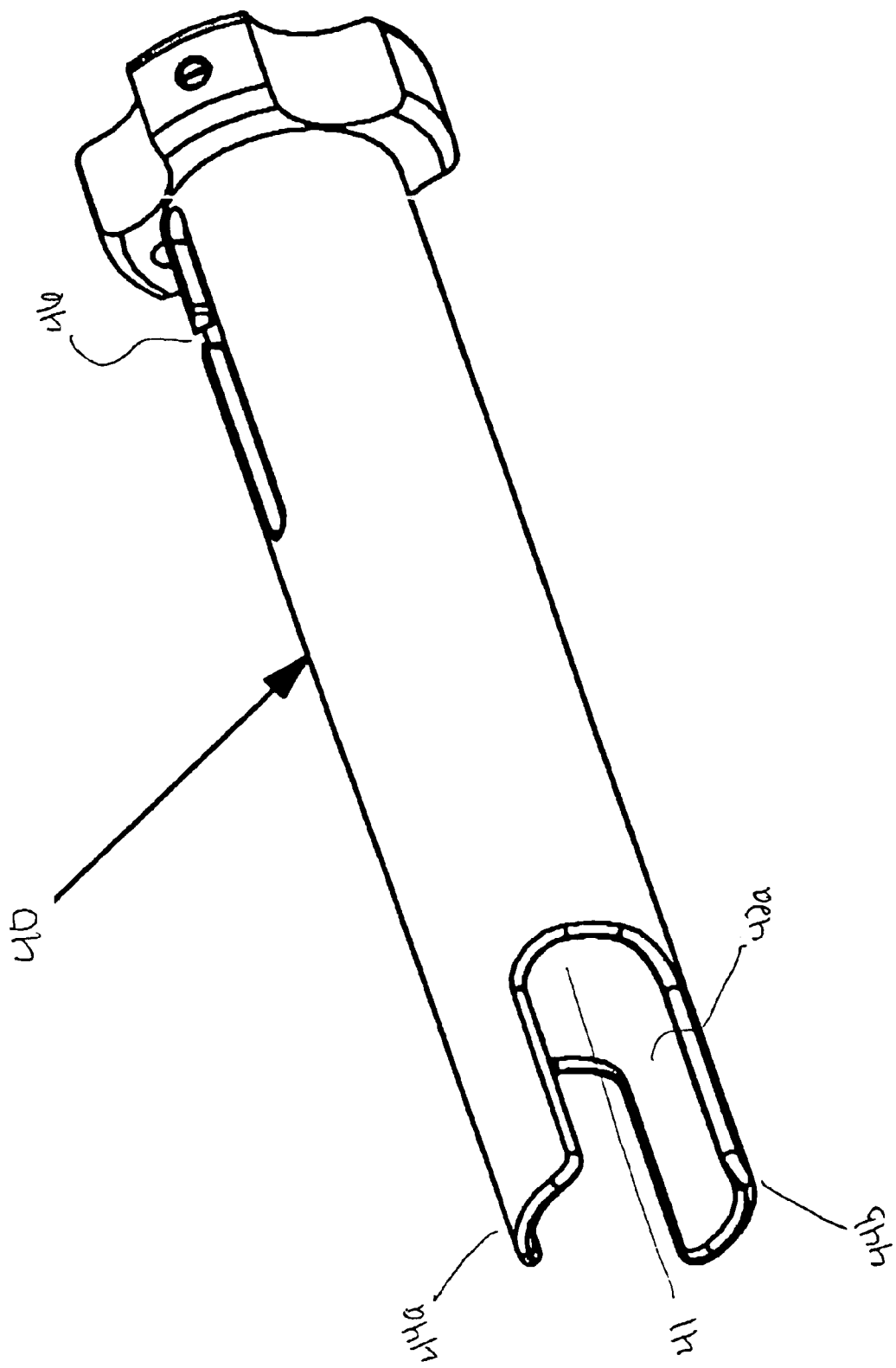
FIG. 8 is a perspective view illustration of the outer sleeve of the device shown in FIG. 1.
Figure 9:
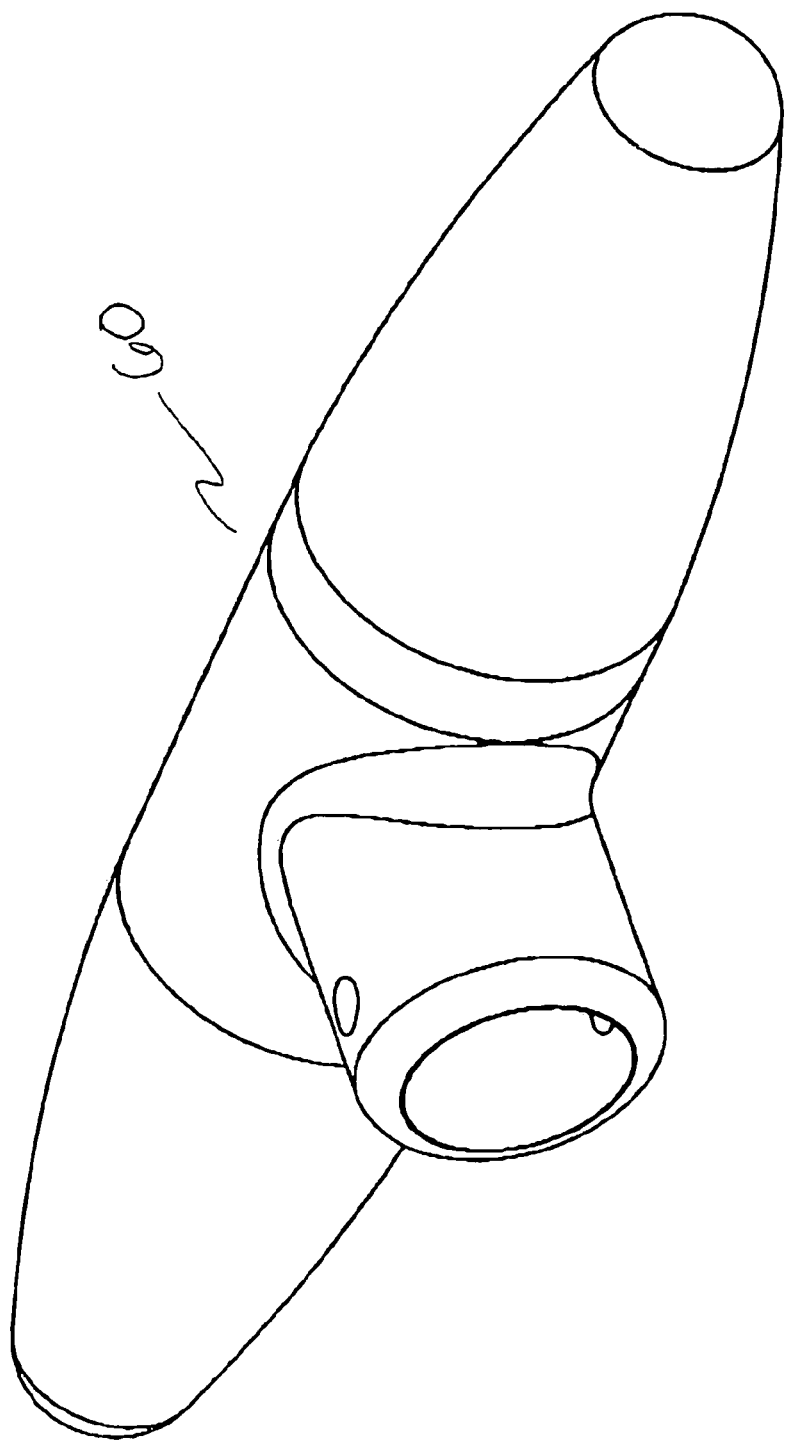
FIG. 9 is a perspective view illustration of the T-handle of the device shown in FIG. 1.
Figure 10A:
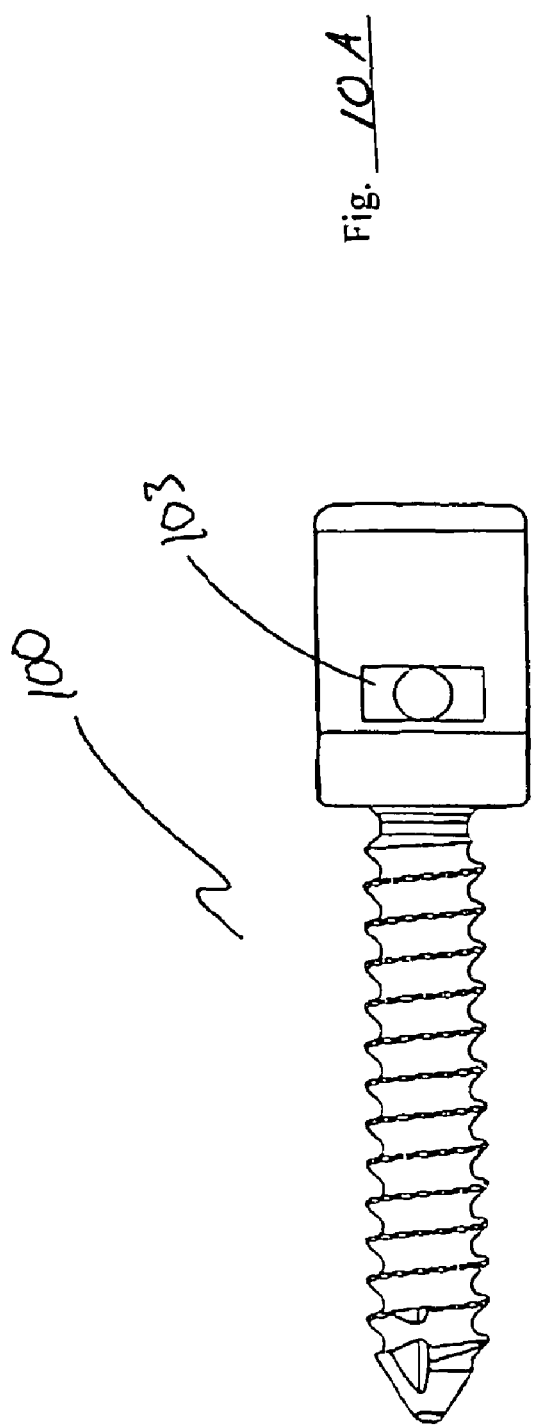
FIGS. 10A and 10B are perspective illustrations of a typical spinal implant.
Figure 10B:
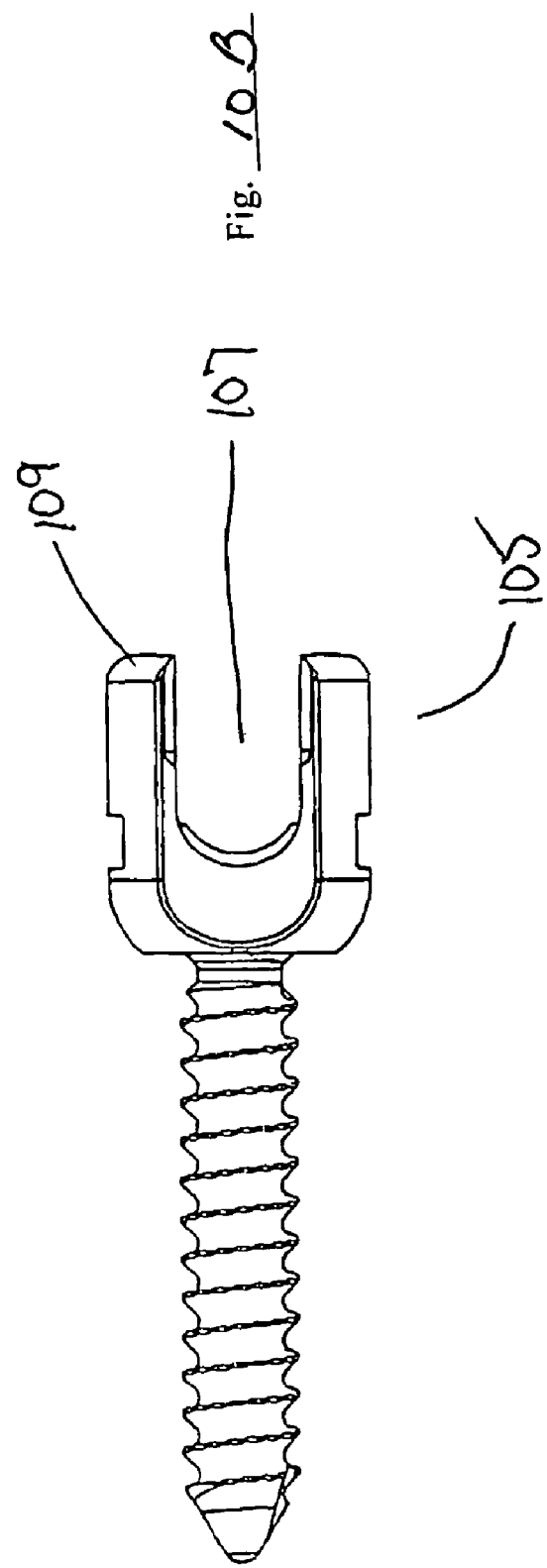

Referring now to FIG. 8, outer sleeve 40 is a hollow substantially cylindrical tube defining an interior channel 41 extending therethrough. The interior channel is sized to allow it to slide along the distal end portion 24b of the body 20 from a first to a second position. In the first position the outer sleeve is raised above the flexible center portion 64 of the branch 66 on the body such that the center portion 64 can expand to grip the implant. In the second position the outer sleeve locks the branches to the implant. The distal end of the outer sleeve has opposed U-shaped channels 42a, 42b configured to allow the tool 10 to capture a spinal rod above the head of the spinal implant while gripping the implant. The arms 44a, 44b located between the U-shaped channels are adapted to slide over the narrow slits 28 of the flexible center portions 64a, 64b when the sleeve is advanced to the second position to lock the branches to the implant. Pin 25 extending from the body projects into a channel 46 on the proximal end portion of the outer sleeve to couple the body and outer sleeve. The channel allows the outer sleeve to move from a first to a second position.

In use, one or more spinal implants 100 are screwed into vertebral bone structures. Typically, where two spinal implants 100 are fastened into adjacent vertebra, a spinal rod is inserted into the rod-receiving portion 107 of each implant. However, due to the alignment of the implants 100, it can be difficult to position the rod within each rod-receiving recess 107. Thus, a rod approximator device is necessary. In use, the outer sleeve is raised in the first position as the spinal rod approximator 10 picks up and retains the spinal implant closure mechanism in the distal end portion 24b of the inserter shaft. The pin on the inserter shaft is visible at the distal end of the channel when the inserter shaft is advanced to pick up the closure mechanism. The pin travels back up the channel to the distal end of the channel when the inserter shaft 30 is retracted inside the body 20 above the U-shaped channels 42a, 42b of the outer sleeve. At this position the projection 38 rests against the rim 56 of the threaded collar.

The tool 10 approaches the head of the spinal implant from above or the side. The flexible center portions 64 of the branches expand to slide over the implant head and spring back to their original position to grip the recesses 103 on the outside of the spinal implant head 105. The outer sleeve 40 slides down into the second position preventing the branches from spreading and disengaging the grip on the implant. The threaded collar 50 is turned to engage the external threads 29 on the body 20 such that the rim 54 of the threaded collar abuts the shoulder 34 of the inserter shaft 30 and advances the shaft. The closure mechanism held in the distal end of the inserter shaft contacts the spinal rod, forcing the rod into the rod-receiving portion 107 of the spinal implant. As the inserter shaft advances axially, the pin follows the channel until it reaches the portion 27 of the channel that branches off at an angle. The pin reaches this position when the rod is seated in the implant. At this point the closure mechanism is properly aligned and the T-handle 60 of the inserter shaft is rotated to insert and lock the closure mechanism into the head of the spinal implant. The inserter shaft is pulled up to disengage the closure mechanism from the holding end and the outer sleeve is slid back to the first position so that the branches of the body are permitted to expand and disengage from the implant simply by pulling the device away from the implant.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A tool for seating a spinal rod in a rod-receiving portion of a spinal implant, the tool comprising:

a body having a proximal end portion and a distal end portion, said distal end portion including a first and second flexible branch for gripping a spinal implant, said flexible branches being biased to a closed position, said flexible branches being spaced-apart a distance to form a first substantially U-shaped recess, said first substantially U-shaped recess opening at an end of the distal end portion and extending proximally from the end;

an inserter shaft slidably received within said body, said inserter shaft having a distal end adapted to hold a closure mechanism for said implant;

a threaded collar, adapted to couple said body and said inserter shaft, wherein said inserter shaft forces a spinal rod into the rod-receiving portion of said implant; and a substantially cylindrical outer sleeve disposed about the distal end portion of the body and movable between a first position and a second position in which the outer sleeve surrounds the branches to inhibit separation of the first and second flexible branches, the outer sleeve including a pair of spaced-apart arms at a distal end of the outer sleeve, the arms defining a second substantially U-shaped recess, the second substantially U-shaped recess aligning with the first substantially U-shaped recess when the outer sleeve is in the second position to accommodate a spinal rod within the first substantially U-shaped recess and the second substantially U-shaped recess.

2. A tool for seating a spinal rod in a rod-receiving portion of a spinal implant, the tool comprising:

a body having a proximal and distal end portion, wherein an interior channel extends between the distal and proximal portions, said distal end portion having flexible branches for gripping a spinal implant and said proximal end portion having external threads, the flexible branches being spaced-apart a distance to form a first substantially U-shaped recess, the first substantially U-shaped recess opening at an end of the distal end portion and extending proximally from the end;

an inserter shaft slidable within said interior channel of the body having a proximal end portion, a distal end portion, and a transition zone located between said distal and proximal end portions, said transition zone having a diameter larger than the proximal end portion, said distal end portion adapted to hold a closure mechanism for the spinal implant;

a collar having an internally threaded hollow body and a central shaft attached to said hollow body, wherein said central shaft limits independent motion between said inserter shaft and said collar, wherein said diameter of the transition zone of the inserter shaft is greater than an inner diameter of the central shaft of the collar, said central shaft of the collar having a distal and a proximal portion, said proximal portion attached to said hollow body and said distal portion extending past said hollow body and having an abutment surface for engaging the transition zone portion of said inserter shaft; and a substantially cylindrical outer sleeve disposed about the distal end portion of the body and movable between a first position and a second position in which the outer sleeve surrounds the flexible branches to inhibit separation of the branches, the outer sleeve including a pair of spaced-apart arms at a distal end of the outer sleeve, the arms defining a second substantially U-shaped recess, the second substantially U-shaped recess aligning with the first substantially U-shaped recess when the outer sleeve is in the second position to accommodate a spinal rod within the first substantially U-shaped recess and the second substantially U-shaped recess.

3. The tool of claim 2 wherein said flexible branches are biased in a closed position.

4. A tool for seating a spinal rod in a rod-receiving portion of a spinal implant comprising:

a body having a proximal and a distal end portion, said distal end portion having branches for gripping a spinal implant, wherein an interior channel extends between the distal and proximal ends, the branches being spaced-apart a distance to form a first substantially U-shaped recess, the first substantially U-shaped recess opening at an end of the distal end portion and extending proximally from the end;

an inserter shaft having a proximal and a distal end portion, said distal end portion adapted to hold a closure mechanism for the spinal implant, wherein said shaft is sized to fit within the interior channel of the body;

a guide mechanism co-operable with said shaft and said body whereby said guide mechanism limits an independent movement of the shaft within the body, the guide mechanism including a channel and a pin adapted to fit within said channel, the channel located on the body and extending parallel to a longitudinal axis of the body, the pin located on said shaft; and a substantially cylindrical outer sleeve disposed about the distal end portion of the body and movable between a first position and a second position in which the outer sleeve surrounds the branches to inhibit separation of the branches, the outer sleeve including a pair of spaced-apart arms at a distal end of the outer sleeve, the arms defining a second substantially U-shaped recess, the second substantially U-shaped recess aligning with the first substantially U-shaped recess when the outer sleeve is in the second position to accommodate a spinal rod within the first substantially U-shaped recess and the second substantially U-shaped recess.

5. The tool of claim 4 wherein a portion of said channel branches off at an angle and reverses direction.

6. The tool of claim 5 wherein a point where said channel branches off corresponds to the point where the spinal rod is fully seated in the implant.

7. The tool of claim 5 wherein said angle is approximately 90 degrees.

8. The tool of claim 4 wherein the pin and channel prevent the shaft from being removed from the body.

9. The tool of claim 4 wherein the independent movement limited is a rotational orientation of the inserter shaft with respect to the body.

10. The tool of claim 4 wherein the independent movement limited is an axial translation of the inserter shaft with respect to the body.

* * * * *